(12) United States Patent
Ryu et al.

(10) Patent No.: US 9,737,206 B2
(45) Date of Patent: Aug. 22, 2017

(54) DEVICE AND METHOD FOR SCREENING FOR BIOACTIVE MATERIALS USING VISUAL RECOGNITION OF ANIMALS

(71) Applicant: GENOMIC DESIGN BIOENGINEERING COMPANY, Daejeon (KR)

(72) Inventors: Jae Ho Ryu, Daejeon (KR); Hae Chul Park, Ansan-si (KR); Sang Yeob Yeo, Daejeon (KR)

(73) Assignee: GENOMIC DESIGN BIOENGINEERING COMPANY, Daejeon (KR)

( * ) Notice: Subject to any disclaimer, the term of this patent is extended or adjusted under 35 U.S.C. 154(b) by 191 days.

(21) Appl. No.: 14/416,015

(22) PCT Filed: Apr. 26, 2013

(86) PCT No.: PCT/KR2013/003623
§ 371 (c)(1),
(2) Date: Jan. 20, 2015

(87) PCT Pub. No.: WO2014/014189
PCT Pub. Date: Jan. 23, 2014

(65) Prior Publication Data
US 2015/0177228 A1    Jun. 25, 2015

(30) Foreign Application Priority Data
Jul. 20, 2012  (KR) .......................... 10-2012-0079142

(51) Int. Cl.
*A61B 5/00* (2006.01)
*A61B 3/02* (2006.01)
*A61B 5/11* (2006.01)
*A61B 3/09* (2006.01)
*A01K 63/00* (2017.01)

(52) U.S. Cl.
CPC .................. *A61B 3/02* (2013.01); *A61B 3/09* (2013.01); *A61B 5/1128* (2013.01); *A61B 5/4848* (2013.01); *A01K 63/003* (2013.01); *A01K 63/006* (2013.01); *A61B 2503/40* (2013.01)

(58) Field of Classification Search
CPC ............................ A01K 63/003; A01K 63/006
See application file for complete search history.

(56) References Cited

PUBLICATIONS

P. Steenbergen et al.: "Patterns of avodance behaviours in the light/dark preference test in young juvenile zebrafish: a pharmacological study," Behavioural Brain Research, 2011, vol. 222, Issue 1, pp. 15-25.

(Continued)

*Primary Examiner* — Max Hindenburg
(74) *Attorney, Agent, or Firm* — Antonio Ha & U.S. Patent, LLC

(57) ABSTRACT

The device for screening for bioactive materials using the visual recognition of animals according to the present invention includes: an accommodating member (100) in which animals administered with a candidate bioactive material are accommodated; an imaging member (200) which captures images of the animals; and a detecting member (300) which reads the images in order to detect the visual recognition reactions of the animals. According to the method of the present invention for screening for bioactive materials using visual recognition of animals, the animals are administered with the candidate bioactive material, and the visual recognition reactions of the animals are detected.

4 Claims, 8 Drawing Sheets

(56) References Cited

PUBLICATIONS

R.E. Blaser et al.: "Behavioral measures of anxiety in zebrafish (*Danio rerio*)," Behavioural Brain Research, 2010, vol. 208, Issue 1, pp. 56-62.
D. Kokel et al.: "Chemobehavioural phenomics and behaviour-based psychiatric drug discovery in the zebrafish," Briefings in Functional Genomics and Proteomics, 2008, vol. 7, No. 6, pp. 483-490.
K. Taylor et al.: "Small molecule screeningin zebrafish: an in vivo approach to identifying new chemical tools and drug leads," Cell Communication and Signaling, 2010, vol. 8, No. 1, Article No. 11, 14 pages.
P. Eimon et al.: "The use of in vivo zebrafish assays in drug toxicity screening," Expert Opinion on Drug Metabolism & Toxicology, 2009, vol. 5, No. 4, pp. 393-401.
A. Avdesh et al.: "Natural Colour Preference in the Zebrafish (*Danio rerio*)," Proceedings of Measuring Behavior, 2010, Eindhoven, The Netherlands, pp. 155-157.
International Search Report issued in International Application No. PCT/KR2013/003623 on Jul. 22, 2013, 3 pages.

DEVICE AND METHOD FOR SCREENING FOR BIOACTIVE MATERIALS USING VISUAL RECOGNITION OF ANIMALS

CROSS REFERENCE TO RELATED APPLICATIONS

This application is a 35 U.S.C. §371 National Phase Entry Application from PCT/KR2013/003623, filed Apr. 26, 2013, and designating the United States, which claims priority under 35 U.S.C. §119 to Korean Patent Application No. 10-2012-0079142 filed Jul. 20, 2012, which is incorporated herein by reference in its entirety.

TECHNICAL FIELD

The present invention relates to a device and method for screening a physiologically active substance based on animal visual perception.

BACKGROUND ART

Photoreceptor cells playing a role in human visual perception are particular subsets of retinal neurons and composed of rod cells and cone cells.

Rod cells contain the visual pigment rhodopsin that absorbs light, and the rod cells perceive the darkness of light (dark adaptation) using this rhodopsin.

Cone cells express photoreceptors capable of sensing red, green and blue wavelengths, and perceive the color of light depending on the extent of the response of the photoreceptors to the light absorbed by the eye.

As described above, the perception process by human vision is very complicated, and varies depending on the human emotional state.

As used herein, the term "physiologically active substance" refers to a substance that enhances or suppresses the function of a living body. A particular component of the substance can influence the biological function of the human body, and particularly, can also influence the visual perceptive function of the human body.

In other words, the fact that a physiologically active substance influences the visual perceptive function of the human body indicates that the physiologically active substance influences the biological function of the human body.

However, the development of a device or method for screening a physiologically active substance, which influences the biological function of the human body, based on the visual cognitive function of test animals, is still insufficient.

DISCLOSURE

Technical Problem

Accordingly, the present invention has been made in order to solve the above-described problems, and an object of the present invention is to provide a device and method for screening a physiologically active substance, which influences the biological function of the human body, based on animal visual perception in a simple manner.

Technical Solution

According to the present invention, a device for screening a physiologically active substance based on animal visual perception includes: an accommodation unit 100 configured to accommodate animals administered with a physiologically active substance candidate; an imaging unit 200 configured to image the animals; and a detection unit 300 configured to detect the visual perception response of the animals by reading the images.

The animals may be fishes capable of distinguishing colors.

The fishes may be zebrafish.

The zebrafish may be zebrafish fry 4 days or more post fertilization.

A first embodiment of the accommodation unit 100 may include: a water tank 110 made of a transparent material and including an inlet portion 111 into which the fishes are to be introduced, a first passage portion 112 formed on one side of the inlet portion 111 and communicating with the inlet portion 111, and a second passage portion 113 formed on the other side of the inlet portion 111 and communicating with the inlet portion 111; a preferred color unit configured to provide a color, for which the fishes have a preference, to the first passage portion 112; and a dislike color unit configured to provide a color, for which the fishes have a dislike, to the second passage portion 113, the accommodation unit 100 allowing the fishes to move to the first passage portion 112 or the second passage portion 113.

In the accommodation unit 100, the preferred color unit may be a first fitting body 120 that has a color for which the fishes have a preference, the first fitting body being fitted around the outside of the first passage portion 112, and the dislike color unit may be a second fitting body 130 that has a color for which the fishes have a dislike, the second fitting body being fitted around the outside of the second passage portion 113.

In the accommodation unit 100, the preferred color unit may be a first irradiating body that irradiates the first passage portion 112 with light having a color for which the fishes have a preference, and the dislike color unit may be a second irradiating body that irradiates the second passage portion 113 with light having a color for which the fishes have a dislike.

A second embodiment of the accommodation unit 100' may include: a water tank 110 made of a transparent material and including an inlet portion 111' into which the fishes are to be introduced, a first passage portion 112' formed on one side of the inlet portion 111' and communicating with the inlet portion 111', and a plurality of second passage portions 113' arranged around the inlet portion 111' and communicating with the inlet portion 111'; a preferred color unit configured to provide a color, for which the fishes have a preference, to the first passage portion 112'; and a dislike color unit configured to provide a color, for which the fishes have a dislike, to the second passage portion 113', the accommodation unit 100 allowing the fishes to move to the first passage portion 112' or the second passage portion 113'.

In the accommodation unit 100', the preferred color unit may be a first fitting body 120' that has a color for which the fishes have a preference, the first fitting body being fitted around the outside of the first passage portion 112', and the dislike color unit may be a second fitting body 130' that has a color for which the fishes have a dislike, the second fitting body being fitted around the outside of the second passage portion 113'.

In the accommodation unit 100', the preferred color unit may be a first irradiating body that irradiates the first passage portion 112' with light having a color for which the fishes have a preference, and the dislike color unit may be a second irradiating body that irradiates the second passage portion 113' with light having a color for which the fishes have a dislike.

The detection unit 300 is configured to detect the visual perception response of the fishes by comparing the number of fishes that moved to the first passage portion with the number of fishes that moved to the second passage portion.

According to the present invention, a method of screening a physiologically active substance based on animal visual perception may include: administering a physiologically active substance candidate to animals; and detecting the visual perception response of the animals.

The animals may be fishes capable of distinguishing colors.

The fishes may be zebrafish.

The zebrafish may be zebrafish fry 4 days or more post fertilization.

The method of screening a physiologically active substance based on animal visual perception may include the steps of: (S10) administering a physiologically active substance candidate to the fishes; (S20) allowing the fishes to choose their preferred color or their dislike color; and (S30) detecting the visual perception response of the fishes by comparing the number of fishes that chose the preferred color with the number of fishes that chose the dislike color.

Advantageous Effects

A device for screening a physiologically active substance based on animal visual perception according to the present invention can screen a physiologically active substance, which influences the biological function of the human body, in a simple manner using the visual perception of animals administered with a physiologically active substance candidate.

Also, the device for screening a physiologically active substance based on animal visual perception according to the present invention can screen a physiologically active substance, which influences the biological function of the human body, using the visual perception of zebrafish which have photoreceptor cells similar to those of humans and to which a physiologically active substance candidate was administered. Thus, the influence of the physiologically active substance on the visual perceptive function of the zebrafish can also be applied as the influence thereof on the biological function of the human body.

Further, the device for screening a physiologically active substance based on animal visual perception according to the present invention has an advantage in that it may use zebrafish fry 4 days or more post fertilization, and thus requires no large space.

The accommodation unit of the present invention includes: the water tank including the inlet portion, the first passage portion and the second passage portion; the first fitting body; and the second fitting body. According to this accommodation unit, a physiologically active substance that can influence the biological function of the human body can be screened based on the visual perceptive function of fishes capable of distinguishing colors. Thus, a physiologically active substance that can influence the biological function of the human body can be more reliably screened based on the visual perceptive function of fishes capable of distinguishing colors.

A method of screening a physiologically active substance based on animal visual perception according to the present invention can conveniently screen a physiologically active substance, which influences the biological function of the human body, based on animal visual perception.

Also, the method of screening a physiologically active substance based on animal visual perception according to the present invention can screen a physiologically active substance, which influences the biological function of the human body, using the visual perception of zebrafish which have photoreceptor cells similar to those of humans. Thus, it can provide information for investigating the influence of a physiologically active substance on the biological function of the human body using zebrafish similar to humans.

Further, the method of screening a physiologically active substance based on animal visual perception according to the present invention has an advantage in that it may use zebrafish fry 4 days or more post fertilization, and thus requires no large space.

MODE FOR INVENTION

Hereinafter, exemplary embodiments of the present invention will be described in further detail with reference to the accompanying drawings.

The accompanying drawings are for illustrative purposes only and are not intended to limit the scope of the present invention.

Figure 1:
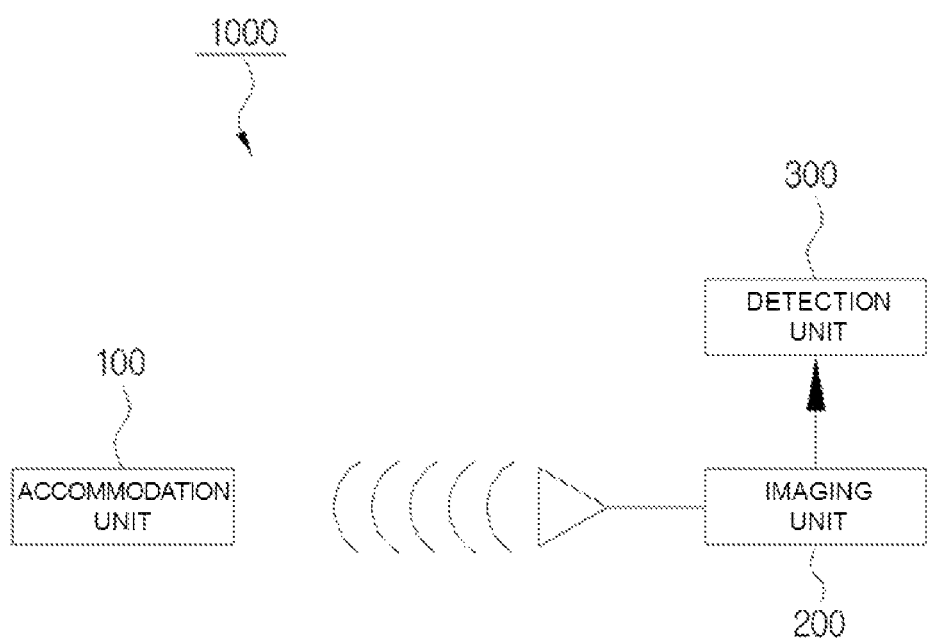
FIG. 1 is a block diagram showing the configuration of a device for screening a physiologically active substance based on animal visual perception according to the present invention.

FIG. 1 is a block diagram showing the configuration of a device for screening a physiologically active substance based on animal visual perception according to the present invention.

As shown in FIG. 1, a device 1000 for screening a physiologically active substance based on animal visual perception according to the present invention includes an accommodation unit 100, an imaging unit 200, and a detection unit 300.

The accommodation unit 100 is configured to accommodate animals administered with physiologically active substance candidates that influence the biological function of the human body. Herein, the animals accommodated in the accommodation unit 100 can show the enhancement or suppression of their visual perceptive function, which is one of the biological functions of the animals, due to administration of physiologically active substance candidates that influence the biological functions of the human body.

The imaging unit 200 is configured to image the animals accommodated in the accommodation unit 100. It may be a known imaging device, and thus the detailed description thereof is omitted.

The detection unit 300 is connected with the imaging unit 200 and is configured to detect the visual perception response of the animals accommodated in the accommodation unit 100 by reading the images taken by the imaging unit 200.

Specifically, the detection unit 300 determines that if the visual perceptive function of the animals administered with a physiologically active substance candidate is normal, the physiologically active substance candidate administered to the animals does not influence the biological function of the animals, and if the visual perceptive function of the animals administered with a physiologically active substance candidate is abnormal, the physiologically active substance candidate administered to the animals influences the biological function of the animals.

Thus, the device for screening a physiologically active substance based on animal visual perception according to the present invention can screen a physiologically active substance, which influences the biological function of the human body, in a simple manner using the visual perception of animals administered with a physiologically active substance candidate.

Meanwhile, the animals accommodated in the accommodation unit 100 may be zebrafish capable of distinguishing color.

Zebrafish are vertebrate animals, and have photoreceptor cells composed of cone cells and rod cells, similar to humans. 55 hours post fertilization of zebrafish, the cone cells and the rod cells are formed, and 4 days post fertilization, the photoreceptor cells are completely formed so that zebrafish have visual perception ability.

Herein, the present invention is characterized in that zebrafish fry 4 days or more post fertilization are accommodated in the accommodation unit 100 in order to miniaturize the accommodation unit 100.

Accordingly, the device for screening a physiologically active substance based on animal visual perception according to the present invention can screen a physiologically active substance, which influences the biological function of the human body, using the visual perception of zebrafish which have photoreceptor cells similar to those of humans and to which a physiologically active substance candidate was administered. Thus, the influence of the physiologically active substance on the visual perceptive function of the zebrafish can also be applied as the influence thereof on the biological function of the human body.

The device for screening a physiologically active substance, in particular, based on animal visual perception according to the present invention has an advantage in that it requires no large space because it screens a physiologically active substance, which can influence the biological function of the human body, using zebrafish fry 4 days or more post fertilization.

The accommodation unit 100 is configured such that fishes, which can distinguish colors and were administered with a physiologically active substance candidate, have a preference or dislike for a particular color, in order to determine the influence of the physiologically active substance candidate on the biological function of the fishes. Embodiments of this configuration will now be described.

Figure 2:
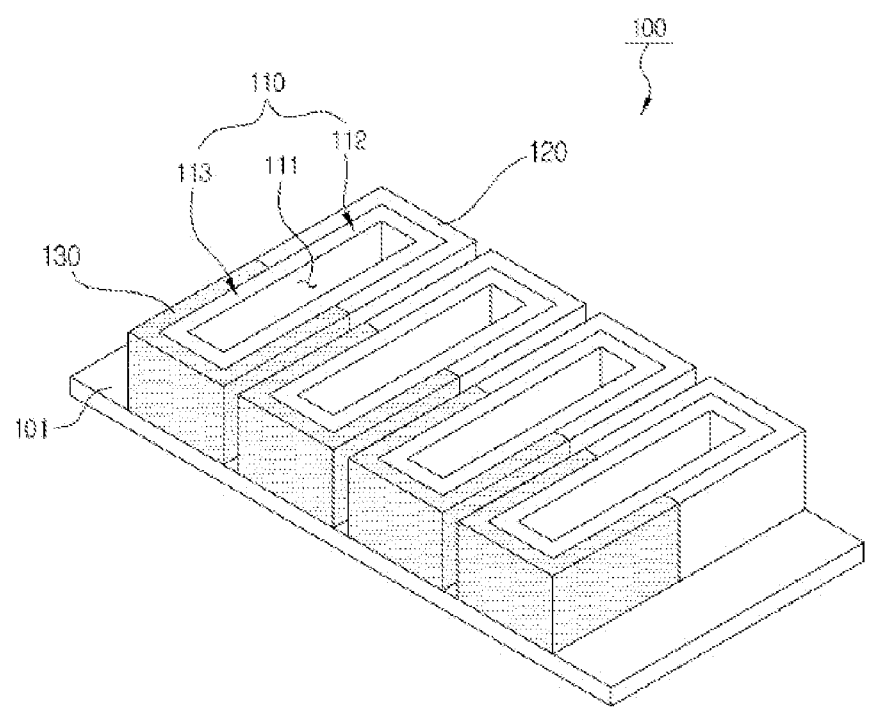
FIG. 2 is a perspective view showing a first embodiment of an accommodation unit according to the present invention.
Figure 3:
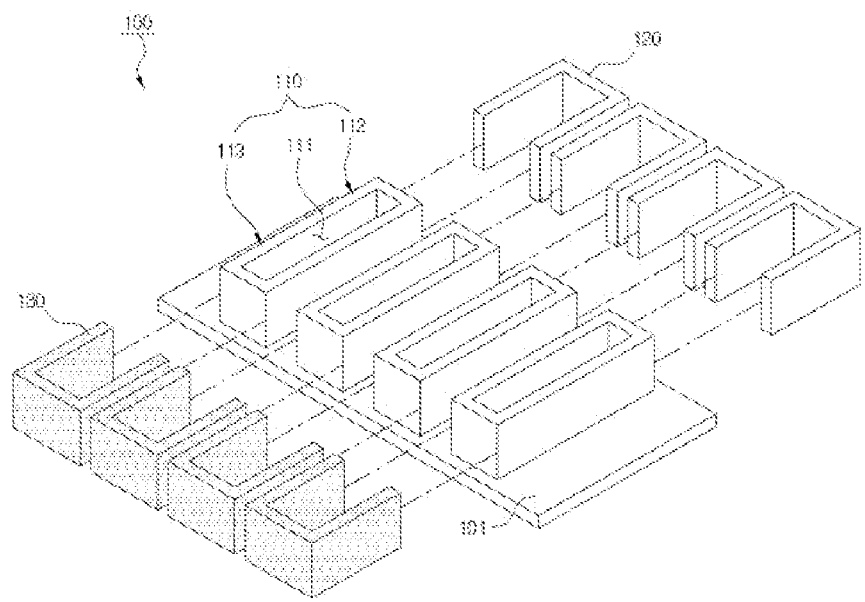
FIG. 3 is an exploded perspective view showing a first embodiment of the accommodation unit according to the present invention.

FIG. 2 is a perspective view showing a first embodiment of the accommodation unit according to the present invention, and FIG. 3 is an exploded perspective view showing a first embodiment of the accommodation unit according to the present invention.

As shown in FIGS. 2 and 3, a first embodiment of the accommodation unit 100 according to the present invention includes a support plate 101, a water tank 110, a preferred color unit, and a dislike color unit.

The support plate 101 has a plate shape.

The water tank 110 is open at the top and made of a transparent material. It is fixed to the support plate 101 at the bottom, and includes an inlet portion 111, a first passage portion 112, and a second passage portion 113.

Meanwhile, the support plate 101 and the water tank 110 are formed integrally with each other.

In addition, a plurality of the water tanks 110 are arranged side by side, and the bottom of each water tank 110 is fixed to the support plate 101.

FIGS. 2 and 3 show an embodiment in which the water tank 110 has a rectangular container shape, but the scope of the present invention is not limited to this embodiment.

The inlet portion 111 is a space formed in the central portion of the water tank 110, and fishes, which can distinguish colors and were administered with a physiologically active substance, are introduced into the inlet portion 111.

The first passage portion 112 is provided at one side of the inlet portion 111 and has a "⊏" shape. It communicates with the inlet portion 111 and functions as a first passage to which fishes introduced into the inlet portion 111 can move.

The second passage portion 113 is provided at the other side of the inlet portion 111 and has a "⊐" shape. It communicates with the inlet portion 111 and functions as a second passage to which fishes introduced into the inlet portion 111 can move.

The preferred color unit is configured to provide a color, for which fishes administered with a physiologically active substance candidate have a preference, to the first passage 112. It is composed of a first fitting body 120 or a first irradiating body (not shown).

The first fitting body 120 has a color for which fishes administered with a physiologically active substance candidate have a preference. It has a "⊏" shape and is fitted around the outside of the first passage portion 112.

The first irradiating body is configured to irradiate the first passage portion 112 with light having a controlled color for fishes administered with a physiologically active substance candidate have a preference.

In other words, the first irradiating body is an illuminator that irradiates a controlled light.

The dislike color unit is configured to provide a color, for which fishes administered with a physiologically active substance candidate have a dislike, to the second passage portion 113. It is composed of a second fitting body 130 or a second irradiating body (not shown).

The second fitting body 130 has a color for which fishes administered with a physiologically active substance candidate have a dislike. It has a "⊐" shape and is fitted around the outside of the second passage portion 113.

The second irradiating body is configured to irradiate the second passage portion 113 with light having a controlled color for fishes administered with a physiologically active substance candidate have a dislike.

In other words, the second irradiating body is an illuminator that irradiates a controlled light.

FIGS. 2 and 3 show the embodiment in which the first passage portion 112, the second passage portion 113, the first fitting body 120, and the second fitting body 130 have a "⊏" shape, but the scope of the present invention is not limited to this embodiment, and the first passage portion 112, the second passage portion 113, the first fitting body 120, and the second fitting body 130 may have other shapes without departing from the technical idea of the present invention.

Meanwhile, fishes introduced into the inlet portion 111 either move to the first passage portion 112 to which a color, for which the fishes have a preference, is provided by the preferred color unit, or move to the second passage portion 113 to which a color, for which the fishes have a dislike, is provided by the dislike color unit. Herein, the wavelength of light having the color for which the fishes have a preference is 380-450 nm (purple) and 450-475 nm (blue), and the wavelength of light having the color for which the fishes have a dislike is 495-570 nm (green) and 570-590 nm. The applicant empirically and experimentally has shown the above-described wavelengths of lights having the colors for which fishes have a preference and a dislike. In addition, the colors for which fishes a preference and a dislike may have other wavelengths.

The detection unit 300 is configured to detect the visual perceptive responses of fishes by reading the movement of fishes taken by the imaging unit 200 and comparing the number of fishes that moved to the first passage portion 112 with the number of fishes that moved to the second passage portion 113. Specifically, the detection unit 300 determines that, if fishes gather together in the first passage portion 112, a physiologically active substance administered to the fishes does not influence the biological function of the fishes, and if the fishes are scattered in both the first passage portion 112) and the second passage portion 113, a physiologically active substance administered to the fishes influences the biological function of the fishes.

This is an embodiment of the method in which the detection unit 300 detects the visual perceptive responses of fishes. In addition to this method, the detection unit 300 of the present invention can detect the visual perceptive responses of fishes by various methods.

As described above, the accommodation unit of the present invention includes: the water tank including the inlet portion, the first passage portion and the second passage portion; the preferred color unit; and the dislike color unit. According to this accommodation unit, a physiologically active substance that can influence the biological function of the human body can be screened based on the visual perceptive function of fishes capable of distinguishing colors. Thus, a physiologically active substance that can influence the biological function of the human body can be more reliably screened based on the visual perceptive function of fishes capable of distinguishing colors.

Figure 4:
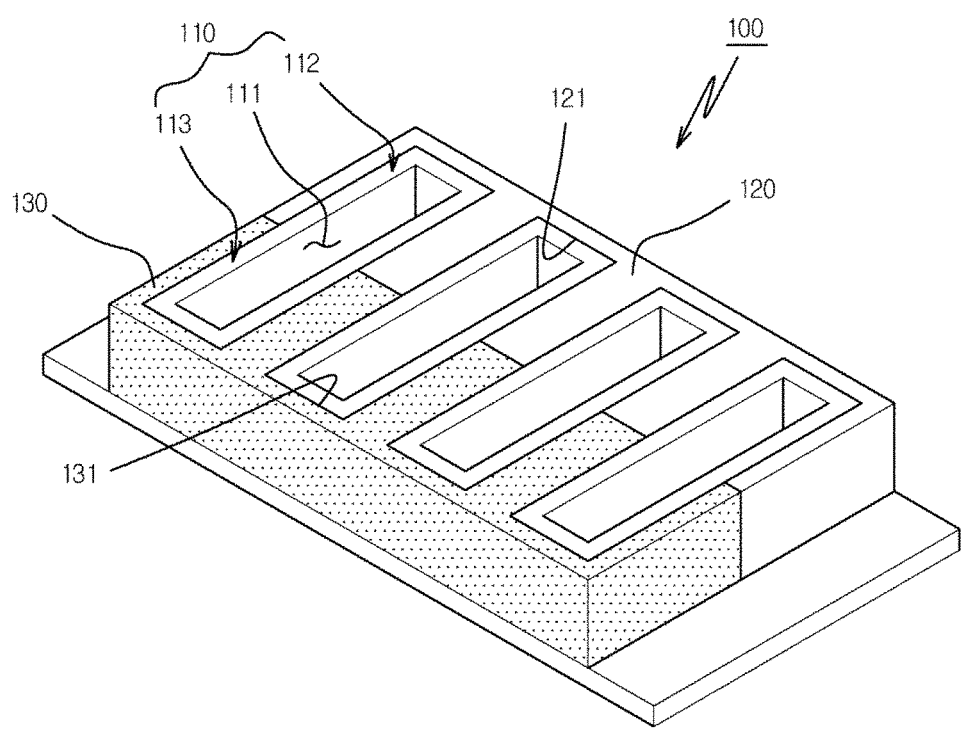
FIG. 4 shows a modification of a first embodiment of an accommodation unit according to the present invention.

FIG. 4 shows a modification of the first embodiment of the accommodation unit according to the present invention.

As shown in FIG. 4, in a modification of the first embodiment of the accommodation unit 100 according to the present invention, the first fitting bodies 120 are connected with one another to form an integral structure, and the second fitting bodies 130 are connected with one another to form an integral structure. Also, the integrally formed first fitting body 120 has a plurality of grooves 121 on its surface facing the integrally formed second fitting body 130, and the integrally formed second fitting body 130 has a plurality of grooves 131 on its surface facing the integrally formed first fitting bodies 120. Thus, the first and second fitting bodies can be more quickly fitted around the water tanks 110.

Herein, the first fitting body 120 and the second fitting body 130 are preferably manufactured by injection molding in terms of easy manufacture.

Figure 5:
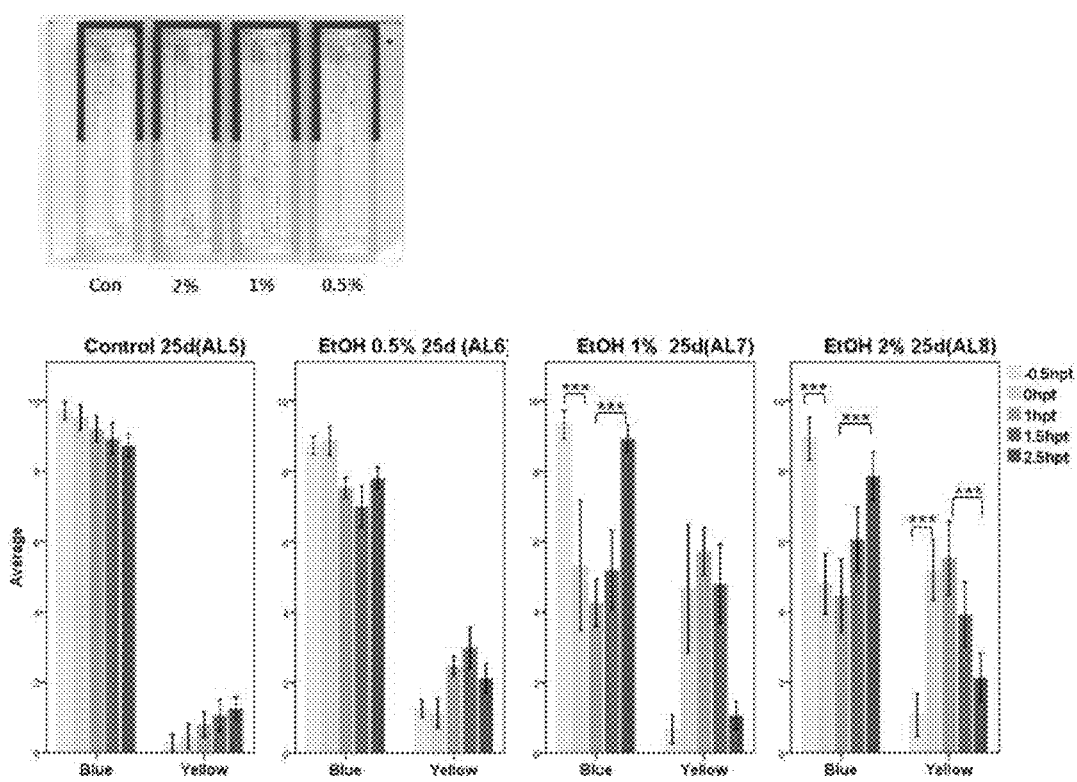
FIG. 5 is a graph showing the results of performing an experimental example using a device for screening a physiologically active substance based on animal visual perception, which includes an accommodation unit according to the first embodiment as shown in FIGS. 2 and 3.

FIG. 5 is a graph showing the results of performing an experimental example using the device for screening a physiologically active substance based on animal visual perception according to the present invention, which includes the accommodation unit according to the first embodiment as shown in FIGS. 2 and 3.

Hereinafter, the present invention will be described in further detail with reference to an experimental example, but the scope of the present invention is not limited to this experimental example.

Experimental Example 1) 5 ml of medium and 10 zebrafish 4 days post fertilization were introduced into the inlet portion 111 of the water tank 110 shown in FIGS. 2 and 3, and the movement of the zebrafish is continuously taken using the imaging unit 200 and stored as an image file (herein, the first fitting body 120 had a blue color for which the zebrafish have a preference, and the second fitting body 130 had a yellow color for which the zebrafish have a dislike.

2) After the medium and the zebrafish were introduced into the inlet portion 111, alcohol as a physiologically active substance candidate was added to the medium at 30-minute intervals so that the alcohol concentration of the medium was 0%, 0.5%, 1% and 2%.

3) The image file stored by the imaging unit 200 was divided into first to fourth image files according to the alcohol concentration.

4) The alcohol component added to the medium was removed using egg water, and the movement of the zebrafish was taken by the imaging unit 200 for 30 minutes, and stored as a fifth image file.

5) The image stored in each of the first to fifth image files was read at 2-minute intervals to count the number of zebrafish in the first passage portion 112 fitted with the first fitting body 120 (preferred color) or the second passage portion 113 fitted with the second fitting body 130 (dislike color).

The experiment as described above was performed, and as a result, the visual perception responses of the zebrafish to the physiologically active substance candidate alcohol could be detected as shown in FIG. 5.

As shown in FIG. 5, as the alcohol concentration of the medium decreased, the number of zebrafish in the first passage portion 112 increased, suggesting that the zebrafish had normal visual perceptive ability, and as the alcohol concentration of the medium increased, the zebrafish were scattered in both the first passage portion 112 and the second passage portion 113, suggesting that the zebrafish had abnormal visual perceptive ability.

Figure 6:
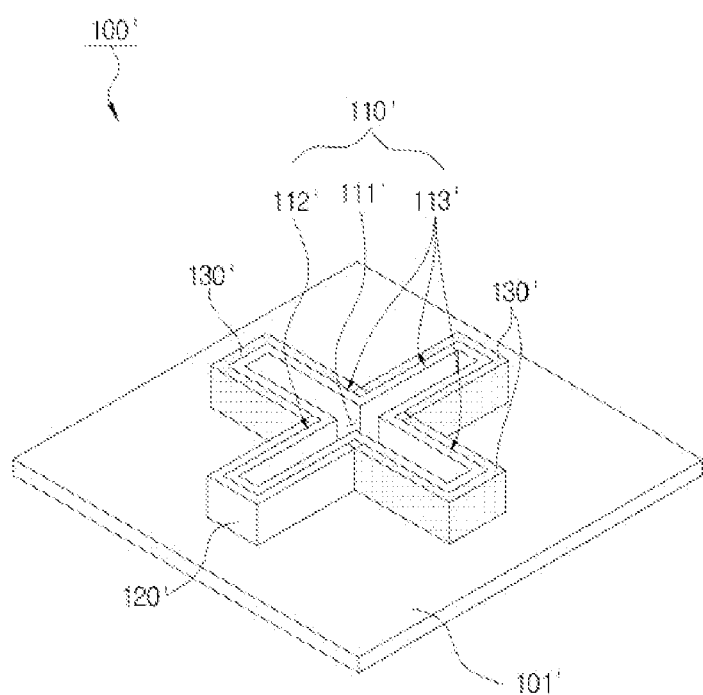
FIG. 6 is a perspective view showing a second embodiment of an accommodation unit according to the present invention.
Figure 7:
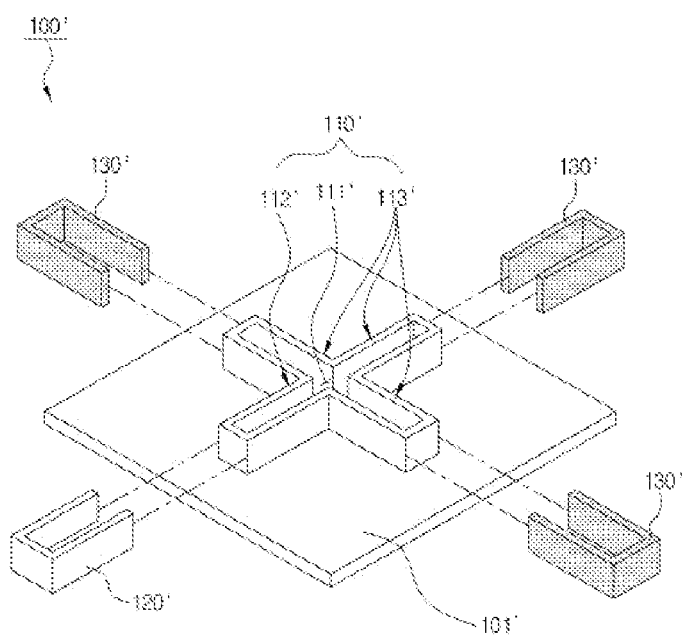
FIG. 7 is an exploded perspective view showing a second embodiment of an accommodation unit according to the present invention.

FIG. 6 is a perspective view showing a second embodiment of the accommodation unit according to the present invention, and FIG. 7 is an exploded perspective view showing a second embodiment of the accommodation unit according to the present invention.

As shown in FIGS. 6 and 7, an accommodation unit 100' according to the present invention includes a support plate 101', a water tank 110', a preferred color unit, and a dislike color unit.

The support plate 101' has a plate shape.

The water tank 110' is open at the top, made of a transparent material, and closed at the bottom by being coupled to the support plate 101'. It includes an inlet portion 111', a first passage portion 112', and a plurality of second passage portions 113'.

Meanwhile, the support plate 101' and the water tank 110' are formed integrally with each other.

FIGS. 6 and 7 shows the embodiment in which the water tank 110' has a cross shape, but the scope of the present invention is not limited to this embodiment.

The inlet portion 111' is a space formed in the central portion of the water tank 110', and fishes, which can distinguish colors and to which a physiologically active substance candidate was administered, are introduced into the inlet portion 111'.

The first passage portion 112' has a '⊏' shape and is disposed on one side around the inlet portion 111'. It communicates with the inlet portion 111' and functions as a first passage to which fishes introduced into the inlet portion 111' can move.

The second passage portions 113' have a '⊏' shape and are arranged around the inlet portion 111'. These communicate with the inlet portion 111' and function as second portions to which fishes introduced into the inlet portion 111' can move.

The preferred color unit is configured to provide a color, for which fishes administered with a physiologically active substance candidate have a preference, to the first passage 112'. It is composed of a first fitting body 120' or a first irradiating body (not shown).

The first fitting body has a color for which fishes administered with a physiologically active substance candidate have a preference. It has a '⊏' shape and is fitted around the outside of the first passage portion 112'.

The first irradiating body 120' is configured to irradiate the first passage portion 112' with light having a controlled color for fishes administered with a physiologically active substance candidate have a preference.

In other words, the first irradiating body is an illuminator that irradiates a controlled light.

The dislike color unit is configured to provide a color, for which fishes administered with a physiologically active substance candidate have a dislike, to the second passage portion 113'. It is composed of a second fitting body 130' or a second irradiating body (not shown).

The second fitting body 130' has a color for which fishes administered with a physiologically active substance candidate have a dislike. It has a '⊏' shape and is fitted around the outside of the second passage portion 113'.

The second irradiating body is configured to irradiate the second passage portion 113' with light having a controlled color for fishes administered with a physiologically active substance candidate have a dislike.

In other words, the second irradiating body is an illuminator that irradiates a controlled light.

FIGS. 6 and 7 show the embodiment in which the first passage portion 112', the second passage portion 113', the first fitting body 120', and the second fitting body 130' have a '⊏' shape, but the scope of the present invention is not limited to this embodiment, and the first passage portion 112', the second passage portion 113', the first fitting body 120', and the second fitting body 130' may have other shapes without departing from the technical idea of the present invention.

Also, FIGS. 6 and 7 show the embodiment in which one first passage portion 112' is formed and a plurality of second passage portions 113' are formed, but the scope of the present invention is not limited to this embodiment, and a plurality of first passage portions 112' may be disposed around the inlet portion 111', and one second passage portion 113' may be disposed around the inlet portion 111'.

Meanwhile, fishes introduced into the inlet portion 111' either move to the first passage portion 112' to which a color, for which the fishes have a preference, is provided by the preferred color unit, or move to the second passage portion 113' to which a color, for which the fishes have a dislike, is provided by the dislike color unit.

According to the second embodiment of the accommodation unit 100' in the present invention, the number of the second passage portions 113' to which fishes introduced into the inlet portion 111' move is larger than that in the first embodiment of the accommodation unit 100' of the present invention, and thus the reliability of detection of the visual perception response of fishes can further be increased.

The detection unit 300 is configured to detect the visual perceptive responses of fishes by reading the movement of fishes taken by the imaging unit 200 and comparing the number of fishes that moved to the first passage portion 112' with the number of fishes that moved to the second passage portion 113'. Specifically, the detection unit 300 determines that, if fishes gather together in the first passage portion 112', a physiologically active substance administered to the fishes does not influence the biological function of the fishes, and if the fishes are scattered in both the first passage portion 112' and the second passage portion 113', a physiologically active substance administered to the fishes influences the biological function of the fishes.

This is an embodiment of the method in which the detection unit 300 detects the visual perception response of fishes. In addition to this method, the detection unit 300 of the present invention can detect the visual perceptive responses of fishes by various methods.

A method of screening a physiologically active substance based on animal visual perception according to the present invention comprises administering a physiologically active substance candidate to animals and detecting the visual perception response of the animals.

Thus, according to the method of screening a physiologically active substance based on animal visual perception according to the present invention, a physiologically active substance that influences the biological function of the human body can be conveniently screened based on animal visual perception.

In the method of screening a physiologically active substance based on animal visual perception according to the present invention, the animals are fishes capable of distinguishing colors, and particularly, are zebrafish.

In addition, according to the method of screening a physiologically active substance based on animal visual perception according to the present invention, a physiologically active substance that can influence the in vivo function of the human body can be screened based on the visual perception of zebrafish having photoreceptor cells similar to those of humans. Thus, the method of the present invention can provide information for detecting the influence of a physiologically active material on the biological function of the human body using zebrafish similar to humans.

In addition, the method of screening a physiologically active substance based on animal visual perception according to the present invention is characterized in that zebrafish, particularly zebrafish fry 4 days or more post fertilization, are used.

Thus, the method of screening a physiologically active substance based on animal visual perception according to the present invention requires no large space, because zebrafish fry 4 days or more post fertilization are used.

Figure 8:
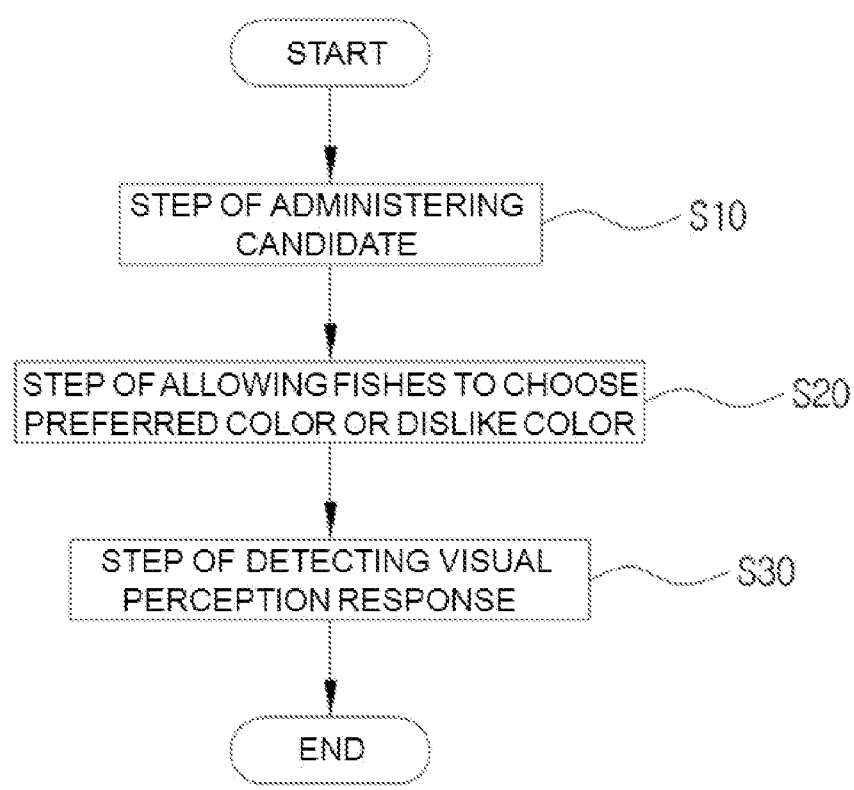
FIG. 8 is a flow chart showing a method of screening a physiologically active substance based on animal visual perception according to the present invention.

FIG. 8 is a flow chart showing the method of screening a physiologically active substance based on animal visual perception according to the present invention.

As shown in FIG. 8, the method of screening a physiologically active substance based on animal visual perception according to the present invention includes the steps of: (S10) administering a candidate; (S20) allowing to choose a preferred color or a dislike color; and (S30) detecting visual perception response.

In step (S10) of administering a candidate, a physiologically active substance candidate is administered to fishes capable of distinguishing colors.

Then, in step (S20) of allowing fishes to have a preference or dislike for a color, the fishes administered with the physiologically active substance candidate are allowed to move to either a first space having a color for which the fishes have a preference, or a second space having a color for which the fishes have a dislike.

Next, in step (S30) of detecting visual perception response, the visual perception response of the fishes is detected by comparing the number of fishes that moved to the first space with the number of fishes that moved to the second space. Specifically, if the fishes gather together in the first space, it is determined that the physiologically active substance candidate did not influence the biological function of the fishes, and if the fishes are scattered in both the first space and the second space, it is determined that the physiologically active substance candidate influenced the biological function of the fishes, thereby detecting the visual perception response of the fishes.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A container for screening a physiologically active substance based on fish's visual perception, comprising:
    a water tank made of a transparent material and comprising an inlet portion into which fishes capable of distinguishing colors are to be introduced, a first passage portion formed on one side of the inlet portion and communicating with the inlet portion, and a second passage portion formed on the other side of the inlet portion and communicating with the inlet portion;
    a preferred color unit fitted so as to cover an outer side surface of the first passage portion and configured to provide light having a preferred color; and
    a dislike color unit fitted so as to cover an outer side surface of the second passage portion and configured to provide light having a dislike color;
    wherein species of the fish is zebrafish,
    wherein the container comprises a plurality of water tanks arranged side by side, and
    wherein the preferred color unit is a fitting body or irradiating body which has a plurality of grooves on a surface thereof facing the dislike color unit and into which the first passage portions of die plurality of water tanks are fitted, and the dislike color unit is a fitting body or irradiating body which has a plurality of grooves on a surface thereof facing the dislike color unit and into which the second passage portions of the plurality of water tanks are fitted.

2. The container of claim 1, wherein the light having the preferred color has a wavelength of 380 nm to 475 nm.

3. The container of claim 1, wherein the light having the dislike color has a wavelength of 495 nm to 590 nm.

4. The container of claim 1, wherein the zebrafish is fry which is more than four days old after fertilization.

* * * * *